United States Patent [19]

Birschbach

[11] Patent Number: 4,745,063
[45] Date of Patent: May 17, 1988

[54] METHOD FOR SEPARATING RENNET COMPONENTS

[75] Inventor: Peter Birschbach, Waukesha, Wis.

[73] Assignee: Sanofi Bio Ingredients, Inc.

[21] Appl. No.: 86,499

[22] Filed: Aug. 17, 1987

Related U.S. Application Data

[63] Continuation-in-part of Ser. No. 913,965, Oct. 1, 1986, abandoned.

[51] Int. Cl.$^4$ .................... C12N 9/64; A23C 9/12; A23C 19/02
[52] U.S. Cl. .................... 435/226; 435/183; 426/36; 426/42; 426/63; 426/271; 530/416
[58] Field of Search .................... 426/36, 34, 42, 63, 426/580, 582, 271; 435/183, 226; 530/416, 417

[56] References Cited

U.S. PATENT DOCUMENTS

| 344,433 | 6/1886 | Blumenthal | 435/226 |
| 3,281,332 | 10/1966 | Munns | 435/226 |
| 3,573,277 | 3/1971 | Grant | 260/231 |
| 3,766,015 | 10/1973 | Dardas | 435/226 |
| 4,136,201 | 1/1979 | Feldman | 426/36 |
| 4,526,868 | 7/1985 | Shasuzzaman et al. | 435/226 |

*Primary Examiner*—Raymond N. Jones
*Assistant Examiner*—Marianne Cintins
*Attorney, Agent, or Firm*—Bayard H. Michael

[57] ABSTRACT

Substantially pure chymosin is separated from rennet extracts by contacting a liquid extract with an anionic exchange medium, preferably a diethylaminoethyl (DEAE) cellulose resin packed in a liquid chromatographic column, either as a static bed or stirred bed. The rennet extract and resin are conditioned so that the resin selectively binds pepsin and chymosin passes through the resin bed and is recovered from the liquid extract from the column. The bound pepsin is periodically removed from the resin by passing a suitable eluant through the resin bed.

16 Claims, No Drawings

METHOD FOR SEPARATING RENNET COMPONENTS

CROSS REFERENCE TO RELATED APPLICATION

This is a continuation-in-part of application Ser. No. 913,965, filed Oct. 1, 1986 now abandoned.

BACKGROUND OF THE INVENTION

The invention relates to methods for separating rennet components and, more particularly, to methods for separating substantially pure chymosin from low quality rennet extracts or the like and using same to adjust the chymosin content of milk clotting enzyme-containing materials to a predetermined level.

Rennet derived from animal tissue, such as the fourth stomach (abomasum) of bovine animals, includes two milk clotting enzymes, chymosin and bovine pepsin. The relative concentration of these two enzymes varies widely depending primarily on the age of the animal at the time of slaughter and/or its diet. For instance, rennet derived from young suckling calves less than 60 days old typically is composed primarily of chymosin, while that derived from an adult animal is composed primarily of bovine pepsin.

When used in the production of cheese, rennets having a high chymosin content generally produce higher yields and superior flavor and texture characteristics. Variations in the chymosin content require changes in the amount of rennet used in order to maintain the same yield and cheese quality. The availability of high chymosin rennet is becoming more limited because of a reduction in the number of calves slaughtered.

IDF Standard 110:1982 describes a chromatographic method for determining chymosin and bovine pepsin content in rennet extracts. Chymosin and pepsin are first applied to a diethylaminoethyl (DEAE) cellulose resin. Sodium chloride solutions of different concentrations are then sequentially passed through the column to obtain a first fraction containing chymosin and a second fraction containing pepsin.

SUMMARY OF THE INVENTION

An object of the invention is to provide an improved method for separating chymosin from a liquid containing the milk clotting enzymes chymosin and pepsin, such as rennet extract, with the capability of obtaining a minimal loss in the original milk clotting activity of either enzyme.

Another object of the invention is to provide such a method by which a fraction containing a chymosin content of 98% or more can be obtained from materials containing relatively smaller amounts of chymosin.

A further object of the invention is to provide a chromatographic column method for separating chymosin from a liquid containing the milk clotting enzymes chymosin and pepsin by which the column requires only periodic elution to remove the bound enzyme.

A still further object of the invention is to provide a method for increasing the chymosin content of milk clotting enzyme-containing materials derived from low quality chymosin-containing tissue.

In the method of the invention, chymosin is separated from a liquid containing the milk clotting enzymes chymosin and pepsin, such as a rennet extract, by contacting an anionic exchange medium, which selectively binds pepsin, with the liquid. Chymosin is recovered from the liquid resulting after contact with the exchange medium and the exchange medium is periodically contacted with a solution for removing pepsin. Prior to the separation step, the rennet extract or the like is adjusted to a pH of about 3.8 to about 5.2, preferably about 4.0 to about 5.0 and most preferably about 4.4 to about 4.6, and to a conductivity of about $2 \times 10^3$ to about $19 \times 10^3$, preferably about $5 \times 10^3$ to about $15 \times 10^3$ and most preferably $8 \times 10^3$ to about $10 \times 10^3$ μmhos. The exchange medium is equilibrated to approximately the same pH and conductivity. Since rennet extracts usually contain substantially smaller amounts of pepsin than chymosin, relatively large amounts of chymosin can be separated before the bound pepsin must be removed from the exchange medium.

In one embodiment, the exchange medium, which preferably is a DEAE cellulose resin, is packed as a bed in a liquid chromatographic column, the rennet extract or the like is passed through the exchange medium bed, chymosin is recovered from the liquid effluent from the column, and an eluant is periodically passed through the exchange medium bed to remove the bound pepsin. Pepsin can be recovered from the eluant effluent.

In another embodiment, the exchange medium bed is agitated or stirred and the rennet extract is added in a batchwise manner.

The chyomsin content of rennet extracts derived from low quality stomachs can be increased to a predetermined level by adding an appropriate amount of the recovered chyomsin thereto.

DESCRIPTION OF THE PREFERRE EMBODIMENTS

The starting material is a liquid containing the milk clotting enzymes chymosin and pepsin. These two milk clotting enzymes may be obtained from a number of different known sources including rennet derived from animal tissue or existing in products consisting of blends or mixtures of enzymes such as a mixture of swine pepsin, bovine pepsin and bovine chymosin. The method is particularly effective for rennets extracted from the fourth stomach (abomasum) of bovine animals and the method will be described in connection with such a rennet extract. It also can be used with material containing chymosin and pepsins (other than bovine pepsin) which bind to an anionic exchange medium at the conditions described below.

The rennet can be extracted from animal tissue by any conventional method. To make the exchange medium selectively bind bovine pepsin, the liquid rennet extract is first adjusted to a pH of about 3.8 to about 5.2 and to a conductivity of about $2 \times 10^3$ to about $19 \times 10^3$ μmhos. There is a tendency for neither chymosin or bovine pepsin to bind to an anionic exchange medium when the pH of the rennet extract is below about 3.8 and both tend to bind to an anionic exchange medium when the pH is above about 5.2. More complete separations of chymosin from bovine pepsin can be obtained at a pH within the rang of about 4.0 to about 5.0 and still more complete separations usually can be obtained at a pH within the range of about 4.4 to about 4.6.

If the conductivity of the rennet extract is below about $2 \times 10^3$ μmhos, the bovine pepsin and other bound molecules, such as pigment, tend to become irreversibly bound to an anionic exchange medium. If the conductivity is above about $19 \times 10^3$ μmhos, there is a tendency for neither bovine pepsin or chymosin to bind to an anionic exchange medium. More complete separations of chymosin from bovine pepsin can be obtained with a conductivity within the range of about $5 \times 10^3$ to about $15 \times 10^3$ and still more complete separations usually can be obtained with a conductivity within the range of about $8 \times 10^3$ to about $10 \times 10^3$ μmhos. At the present time, it appears that the optimum pH and conductivity are about 4.5 and $9 \times 10^3$ μumhos, respectively.

The pH of the rennet extract can be adjusted to the desired level by adding an appropriate amount of a suitable food safe acid, such as dilute sulfuric acid (if the initial pH is above the desired level), or a suitable food safe base, such as ammonium hydroxide (if the pH is below the desired level). The conductivity of the rennet extract, as measured by a conductivity bridge or the like, can be adjusted to a desired level by adding an appropriate amount of a suitable food safe salt, such as sodium chloride (if the initial conductivity is below the desired level), or by diluting with deionized water (if the conductivity is above the desired level).

The anionic exchange medium can be any type capable of being equilibrated to selectively bind bovine pepsin and then release the bound bovine pepsin upon being contacted with a food safe eluant. Suitable exchange media include ones having an inert, insoluble matrix, such as cellulose, acrylic polymers and the like, and into which anionic functional groups, such as amino, alkyl amino, guanidino, and quaternary ammonium groups, have been introduced. The matrix should have a structure which is open or loose enough so as not to become plugged with particles in the rennet extract and to permit a reasonable throughput when used in a liquid chromatographic column as described below.

Cellulose resins having an open, fibrous matrix are preferred. Representative suitable cellulose resins are disclosed in U.S. Pat. No. 3,573,277 which is incorporated herein by reference. DEAE cellulose resins have been found to be particularly effective.

When a DEAE cellulose resin is used as the exchange medium, it is precycled in a conventional manner prior to use. For example, the resin is stirred into 0.5 N hydrochloric acid for thirty minutes and the supernatant is decanted. The resin is then rinsed with deionized water until the supernatant has a pH of 4.0. The resin is then stirred in 0.5 N sodium hydroxide for thirty minutes and the supernatant decanted. The resin is then rinsed with deionized water until the supernatant has a pH of 8.0.

The precycled exchange medium is equilibrated to a pH and conductivity within above ranges so that bovine pepsin is selectively attracted to the exchange medium. Equilibration can be accomplished by washing the exchange medium with a buffer solution having the desired pH and conductivity. For example, a typical equilibrating solution can consist of an aqueous solution which contains 0.5% (weight/volume) sodium benzoate and a sufficient amount of sodium chloride to give a conductivity of $9 \times 10^3$ μumhos and to which dilute sulfuric acid is added to adjust the pH to 4.5. Equilibration is continued until the decanted supernatant has the desired pH and conductivity.

The precycled and equilibrated exchange medium can be packed into a conventional chromatographic column including a porous support, such as a screen, for a bed of the exchange medium, and a valve for controlling a continuous flow of the rennet extract through the column.

The adjusted rennet extract is introduced into the column, passes through the static resin bed and the flow of the chymosin-containing effluent is adjusted with the control valve to allow sufficient contact between the rennet extract and the resin for the bovine pepsin to bind onto the resin. This time can be determined by analyzing the effluent in a conventional manner for chymosin and bovine pepsin. If the amount of extract introduced into the column or the rate at which it passes through the resin bed is too high, a portion of the bovine pepsin will not bind on to the resin (i.e., there is an incomplete separation between bovine pepsin and chymosin) and this will be reflected by the presence of larger amounts of bovine pepsin in the effluent.

The volume of and the rate at which the rennet extract is introduced into column can be determined by routine experimentation and depends on the volume of the anionic exchange medium in the column, the enzyme binding capacity of the particular exchange medium used, concentration of bovine pepsin in the rennet extract, and concentration of non-enzyme contaminants in the rennet extract (e.g., pigment) which become bound to the exchange medium. For applications where less than substantially complete separation of chymosin is acceptable, the flowrate of the rennet extract through the column can be increased. This decreases the contact time and results in a less complete separation.

Such a static bed procedure may have shortcomings when used with some crude rennet extracts. It may be difficult to maintain an acceptable flowrate through the column, particularly when a viscous extract is being used. The upper layer of the exchange medium can become saturated with insoluble materials, such as fats, mucins, etc., causing a reduction in flowrate. Channeling of the exchange medium may occur, resulting in a reduction of the contact between the exchange medium and the enzymes and a decrease in bovine pepsin binding.

These shortcomings can be minimized by using a stirred-bed column. Such a column is similar to a static bed column, except that the exchange medium bed is agitated or stirred, the extract is added in a batchwise manner and the inside diameter of the column usually is somewhat larger for the same volume of exchange medium.

When a stirred-bed chromatographic column is used, the precycled and equilibrated exchange medium is introduced into a column having a porous support and a suitable agitator, such as an air-driven paddle type agitator. A volume of adjusted rennet extract is introduced into the column and the extract-exchange medium mixture is agitated for a sufficient time to obtain intimate contact therebetween and bind bovine pepsin to the exchange medium. The contact time required for good separations is usually shorter for a stirred-bed column than for a static bed column. Agitation is stopped after the desired contact time, the liquid phase either drained or decanted from the column and another volume of rennet extract is introduced into the column. This cycle can be repeated until the binding capacity of the exchange medium has been exhausted or the entire rennet extract volume has been introduced into the column.

Substantially pure chymosin can be recovered from the effluent or liquid extract from the column by a suitable purification technique. For example, the effluent can be adjusted to a pH of about 5.6 and then introduced into a chromatographic column wherein chymosin is bound to the exchange medium and subsequently removed with a suitable food safe eluant.

This chymosin can be added to rennet extracts to increase the chymosin content to a predetermined level. Thus, low quality rennet extracts can be upgraded and the chymosin content of either high or low quality rennet extracts can be adjusted to a standard value and thereby eliminate performance variations in cheese making processes. For example, the method of the invention can be used to separate chymosin from rennet extracts containing as little as about 15% chymosin (based on total milk clotting activity) and up to about 85% and then added to extracts having the same range of chymosin concentrations to increase the chymosin content to a desired level.

The resin bed preferably is periodically rinsed to remove unbound foreign materials. The resin bed preferably is agitated during the rinsing cycle to enhance removal of such foreign materials. The effluent from the rinsing cycle preferably is collected in a separate receptacle.

An eluant is periodically introduced into the column to remove the bound bovine pepsin from the resin and the effluent collected in a separate receptacle. Flow of the eluant through the resin bed is continued until little or no milk clotting activity is detected in the effluent. Bovine pepsin can be concentrated from the elution effluent by ultrafiltration, reverse osmosis or other suitable concentration techniques.

The elution solution preferably is aqueous-based and contains a food safe, water soluble salt having reasonable dissociation characteristics. Suitable salts include sodium chloride, sodium phosphate and sodium acetate. A particularly effective eluant for DEAE cellulose resins is a 10% sodium chloride solution adjusted to a pH of about 4.4 to about 4.6. Elution should be performed prior to the time the resin becomes loaded with bovine pepsin to the point where it is no longer capable of binding bovine pepsin.

Following elution, the resin bed can be equilibrated as described above to be made ready for the next separation cycle.

The following examples are presented to exemplify preferred embodiments of the invention and should not be construed as limitations thereof. In the examples, the enzyme compositions were determined by the method described in Collin et al., "A Determination of Chymosin and Bovine Pepsin A in Commercial Rennets and Pepsin", *Milchwisqenschaft* 36(1) 1981.

EXAMPLE 1

A rennet extract obtained from the fourth stomach of veal calves was adjusted to a pH of 4.5 and a conductivity of $7.8 \times 10^3$ μmhos and was assayed for milk clotting activity and enzyme composition. 100 g of DEAE cellulose resin was precycled in accordance with the general procedure described above and then equilibrated with a solution containing 0.5% (weight/volume) sodium benzoate to which sodium chloride was added to adjust the conductivity to $8.0 \times 10^3$ μmhos and dilute sulfuric acid was added to adjust the pH to 4.5.

The equilibrated resin was packed in a glass chromatographic column including a porous bed support and a stopcock for regulating outflow. The adjusted rennet extract was introduced into the column at a flow rate of about 10 ml/min and the effluent was collected and assayed for enzyme composition. The resin was rinsed with 200 ml of the equilibration solution after 1,000 ml of the rennet extract had been separated. The rinse effluent was collected and assayed for milk clotting activity.

Following this rinse, the column was eluted with a 10% sodium chloride solution adjusted to a pH of 4.5. Elution was continued until a milk clotting activity of less than 1.0 unit/ml was detected in the elution effluent. The elution effluent was collected and assayed for milk clotting activity and enzyme composition.

The results from this test are summarized in Table I.

TABLE I
ASSAY OF RENNET AND EFFLUENTS

| | Milk Clotting Activity, units | Enzyme Composition, act.[1] | |
|---|---|---|---|
| | | Chymosin | Pepsin[2] |
| Rennet Extract | 18,500 | 85.6 | 14.4 |
| Separation Effluent | 15,631 | >99 | <1 |
| Rinse Effluent | 213 | — | — |
| Elution Effluent | 2,678 | 11.3 | 88.7 |

Notes:
[1] percentage of total milk clotting activity
[2] Bovine pepsin

EXAMPLE 2

A rennet extract obtained from the fourth stomach of veal calves was adjusted to a pH of 4.5 and a conductivity of $9.0 \times 10^3$ μmhos and assayed for milk clotting activity and enzyme composition. 200 kg of a DEAE cellulose resin was precycled in accordance with the general procedure described above and then equilibrated with a solution containing sodium benzoate to which sodium chloride was added to give a conductivity of $9.0 \times 10^3$ μmhos and dilute sulfuric acid was added to adjust the pH to 4.5.

The equilibrated resin was packed into a fiberglass chromatographic column having an inside diameter of 122 cm and a height of 183 cm and including a motor-driven agitator, a porous resin bed support and a control valve. The adjusted rennet was introduced into the column at a flow rate of approximately 25 l/m and the effluent was collected. After 23,000 l of the rennet extract had been flowed through the column, approximately 1900 l of the equilibrating solution was introduced into the column with the agitator operating, to wash the resin. Introduction of the rennet extract was continued after completion of this washing cycle. A second washing cycle was performed after another 19,300 l of the rennet extract had been introduced and a third washing cycle was performed after a further 19,840 l of the extract had been introduced. The wash effluent was collected and combined with the separation effluent. These combined effluents were assayed for milk clotting activity and enzyme composition.

After completion of the third wash cycle, the column was eluted with a 10% sodium chloride solution adjusted to a pH of 5.6. Elution was continued until a milk clotting activity of less than 1.0 unit/ml was detected in the elution effluent and the elution effluent was assayed for milk clotting activity and enzyme composition.

The results from this test are summarized in Table II.

TABLE II
ASSAY OF RENNET AND EFFLUENTS

| | Milk Clotting Activity, units | Enzyme Composition, act.[1] | |
|---|---|---|---|
| | | Chymosin | Pepsin[2] |
| Rennet | $6.11 \times 10^8$ | 87.1 | 12.9 |
| Separation and Wash Effluent | $5.247 \times 10^8$ | >99 | <1 |
| Elution Effluent | $0.819 \times 10^8$ | 8.8 | 91.2 |

Notes:
[1] percentage of total milk clotting activity
[2] Bovine pepsin

From these results, it can be seen that a fraction containing substantially only chymosin and a negligible amount of bovine pepsin can be obtained from a rennet extract by the process of the invention with little or no loss in the milk clotting activity.

EXAMPLE 3

Two series of tests were made to determine the effectiveness of the separation between chymosin and bovine pepsin in a rennet extract with variations in the pH and conductivity of an equilibrated resin and an adjusted rennet extract. The conductivity was maintained at $9 \times 10^3$ μumhos and pH varied in one series and the pH maintained at 4.5 and the conductivity varied in the other.

For each test 25 g of a DEAE cellulose resin was precycled according to the general procedure described above and then equilibrated to the desired pH and conductivity. The equilibrated resin was packed into a glass chromatographic column including a porous bed support and a stopcock to regulate flow. A rennet extract, obtained from the fourth stomach of veal calves, was adjusted to the same pH and conductivity as the equilibrated resin and assayed for milk clotting activity and enzyme composition. 1000 ml of the adjusted extract was introduced into the column and flowed through the resin bed at a rate of approximately 4 ml/min. and the effluent was collected. The column was rinsed with 100 ml of the solution used to equilibrate the resin and the rinse effluent was collected and combined with the separation effluent.

Following this rinse, the column was eluted with 250 ml of a 10% sodium chloride solution adjusted to a pH of 5.6 and the elution effluent was collected. The combined separation and rinse effluents and the elution effluent were separately assayed for milk clotting activity and enzyme composition and the volumes of both were measured.

The results from these tests are summarized in Table III. From the test results, it can be seen that no significant separation between chymosin and bovine pepsin was obtained at a pH of 3.7, while there was a significant increase in the chymosin content in the separation and rinse effluents when the pH was raised to 4.0. There was no significant separation between chymosin and bovine pepsin and both bound to the resin at a pH of 5.3, while there was a significant increase in the chymosin content and the separation and rinse effluents when the pH was raised to 5.0. At a conductivity of $2 \times 10^3$ μmhos there was an increase in the chymosin content in the separation and rinse effluent; however, the total enzyme recovery was less than 60%, indicating that a significant amount of the enzyme was irreversibly bound to the resin. There was no significant separation between chymosin and bovine pepsin at a conductivity of $20 \times 10^3$ μumhos, while there was very good separations at conductivities of $5 \times 10^3$ and $15 \times 10^3$ μmhos.

TABLE III
ENZYME SEPARATIONS WITH VARIATIONS OF pH AND CONDUCTIVITY

| | | Rennet Extract | | | Separation & Rinse Effluents | | | Elution Effluent | | |
|---|---|---|---|---|---|---|---|---|---|---|
| pH | Conduct, × $10^3$ umhos | Vol., ml | Enzyme[1] Composition | MCA[2] units/ml | Vol., ml | Enzyme Composition | MCA[2] units/ml | Vol., ml | Enzyme Composition | MCA[2] units/ml |
| 3.7 | 9.0 | 1000 | 78% C 22% P | 10.6 | 1140 | 79% C 21% P | 7.4 | 240 | n.p. | 1.3 |
| 4.0 | 9.0 | 1000 | 81% C 19% P | 7.2 | 1120 | 94% C 6% P | 5.8 | 265 | n.p | 1.8 |
| 5.0 | 9.0 | 1000 | 78% C 22% P | 10.8 | 1130 | 100% C 0% P | 8.0 | 285 | n.p. | 11.6 |
| 5.3 | 9.0 | 1000 | 81% C 19% P | 6.8 | 1090 | n.p.[3] | 0.9 | 235 | 80% C 20% P | 23.3 |
| 4.5 | 2.0 | 1000 | 22% C 78% P | 2.4 | 1120 | 98% C 2% P | 0.5 | 290 | n.p. | 2.8 |
| 4.5 | 5.0 | 1000 | 22% C 78% P | 3.9 | 1120 | n.p. | 1.0 | 265 | 2% C 98% P | 9.5 |
| 4.5 | 15.0 | 1000 | 82% C 18% P | 15.1 | 1100 | 98% C 2% P | 11.6 | 255 | n.p. | 4.9 |
| 4.5 | 20.0 | 1000 | 22% C 78% P | 3.8 | 1100 | 21% C 79% P | 3.2 | 260 | n.p. | 2.6 |

Notes:
[1] C = chymosin; P = Bovine pepsin
[2] MCA = milk clotting activity
[3] n.p. = not performed

I claim:
1. A method for separating chymosin from a liquid containing the milk-clotting enzymes chyomsin and pepsin comprising the steps of:
   adjusting the enzyme-containing liquid to a pH of about 3.8 to about 5.2 and to a conductivity of about $2 \times 10^3$ to about $19 \times 10^3$ μumhos;
   equilibrating an anionic exchange medium bed to a pH of about 3.8 to about 5.2 and to a conductivity of about $2 \times 10^3$ to about $19 \times 10^3$ μumhos;
   contacting the equilibrated exchange medium with the adjusted enzyme-containing liquid to bind pepsin onto the exchange medium;
   recovering chymosin in the liquid resulting after contact with the exchange medium bed; and
   periodically contacting the exchange medium with a solution for removing the bound pepsin therefrom.
2. A method according to claim 1 wherein:
   the exchange medium is packed in a liquid chromatographic column;

the adjusted enzyme-containing liquid is passed through the exchange medium bed;

chymosin is recovered from the liquid effluent from the column; and the pepsin-removing solution is an eluant passed through the exchange medium bed.

3. A method according to claim 2 wherein said bed is substantially static and the adjusted enzyme-containing liquid is continuously flowed therethrough.

4. A method according to claim 2 wherein
a batch of the adjusted enzyme-containing liquid is introduced into the column;
said bed is agitated for a sufficient time to intimately contact the exchange medium with the enzyme and bind the pepsin thereto; and
removing a liquid extract containing chymosin from the column.

5. A method according to claim 1 wherein the enzyme-containing liquid is a rennet extract.

6. A method according to claim 5 wherein the rennet extract is derived from bovine abomasums.

7. A method according to claim 5 wherein the exchange medium is a diethylaminoethyl cellulose resin.

8. A method according to claim 7 wherein the enzyme-containing liquid and the exchange medium are adjusted to a pH of about 4.0 to about 5.0.

9. A method according to claim 8 wherein the enzyme-containing liquid and the exchange medium are adjusted to a pH of about 4.4 to about 4.6.

10. A method according to claim 5 wherein the enzyme-containing liquid and the exchange medium is adjusted to a conductivity of about $5 \times 10^3$ to about $15 \times 10^3$ $\mu$mhos.

11. A method according to claim 10 wherein the enzyme-containing liquid and the exchange medium is adjusted to a conductivity of about $8 \times 10^3$ to about $10 \times 10^3$ $\mu$mhos.

12. A method according to claim 1 including the step of rinsing the exchange medium bed with a liquid after a predetermined quantity of the enzyme-containing liquid has been passed therethrough.

13. A method according to claim 12 wherein the rinse liquid is the same as that used for equilibrating the exchange medium.

14. A method for increasing the chyomsin content of a milk clotting enzyme-containing material derived from low quality chyomsin-containing tissue to a predetermined level comprising the steps of:
assaying the enzyme-containing material to determine the chyomsin content thereof; and
adding to the enzyme-containing material a sufficient amount of chyomsin prepared in accordance with the method in claim 1 to increase the total chyomsin content to said predetermined level.

15. A method according to claim 14 wherein the enzyme-containing material is a rennet extract.

16. A method according to claim 15 wherein the rennet extract is derived from bovine abomasums.

* * * * *